United States Patent [19]
Gast et al.

[11] Patent Number: 5,984,890
[45] Date of Patent: Nov. 16, 1999

[54] MEDICAL DEVICE FOR THE PLACEMENT OF SOLID MATERIALS

[75] Inventors: Michael J. Gast, Phoenixville; Neil W. Miller, Newtown; John M. Patton, Coatesville, all of Pa.

[73] Assignee: American Home Products Corporation, Madison, N.J.

[21] Appl. No.: 08/937,318

[22] Filed: Sep. 22, 1997

Related U.S. Application Data

[60] Provisional application No. 60/026,911, Sep. 27, 1996, abandoned.

[51] Int. Cl.$^6$ .................................................... A61M 31/00
[52] U.S. Cl. ................................................. 604/60; 604/57
[58] Field of Search ............................. 606/117; 604/116, 604/59–64, 57

[56] References Cited

U.S. PATENT DOCUMENTS

| | | |
|---|---|---|
| 2,577,481 | 12/1951 | Piechaczek et al. . |
| 2,660,169 | 11/1953 | Malm . |
| 3,324,854 | 6/1967 | Weese . |
| 4,086,914 | 5/1978 | Moore . |
| 4,147,164 | 4/1979 | Behney . |
| 4,402,308 | 9/1983 | Scott . |
| 4,403,987 | 9/1983 | Gottinger . |
| 4,451,253 | 5/1984 | Harman . |
| 4,661,103 | 4/1987 | Harman . |
| 4,753,636 | 6/1988 | Free . |
| 4,820,267 | 4/1989 | Harman . |
| 4,846,793 | 7/1989 | Leonard . |
| 4,871,094 | 10/1989 | Gall . |
| 4,900,304 | 2/1990 | Fujioka et al. . |
| 4,941,874 | 7/1990 | Sandow et al. . |
| 4,966,589 | 10/1990 | Kaufman . |
| 4,994,028 | 2/1991 | Leonard et al. . |
| 5,024,665 | 6/1991 | Kaufman . |
| 5,192,271 | 3/1993 | Kalb et al. . |
| 5,300,079 | 4/1994 | Niezink et al. . |
| 5,385,554 | 1/1995 | Brimhall . |
| 5,395,317 | 3/1995 | Kambin . |

*Primary Examiner*—Corrine McDermott
*Assistant Examiner*—Kent Gring
*Attorney, Agent, or Firm*—Steven R. Eck

[57] ABSTRACT

The present invention provides improved devices for inserting solid materials under a tissue, the devices particularly containing a penetration guide means designed to facilitate the implantation by limiting the insertion of the implants to positions under and substantially parallel to the plane of the tissue.

7 Claims, 2 Drawing Sheets

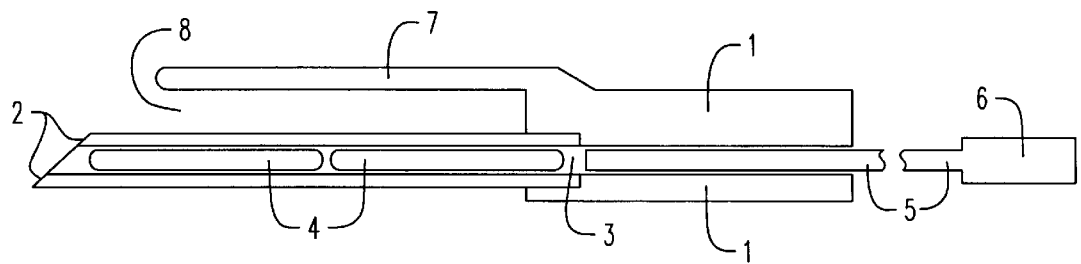
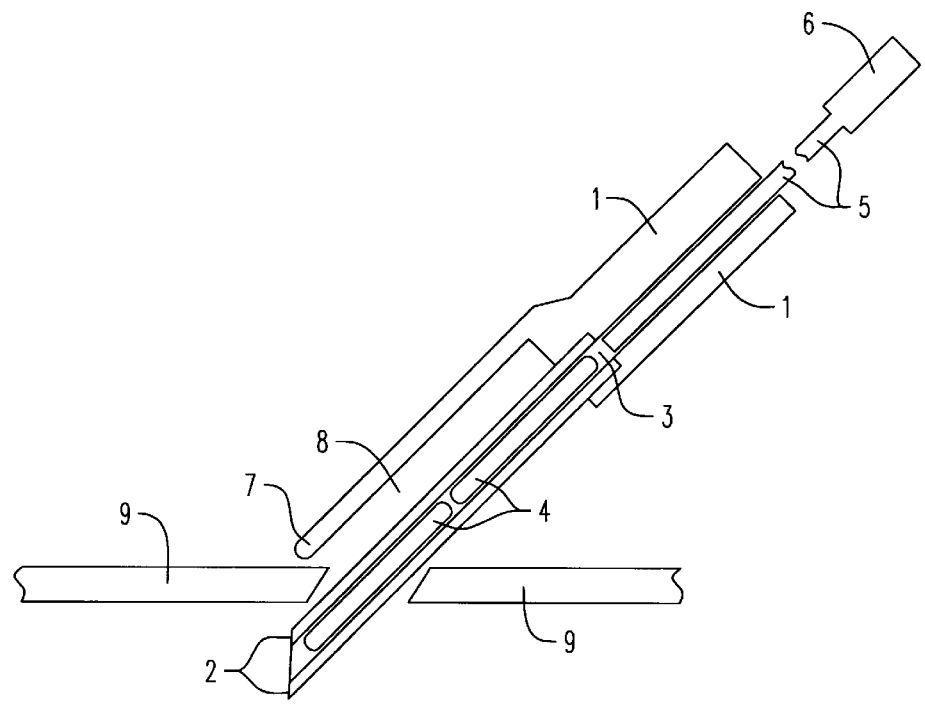

5,984,890

MEDICAL DEVICE FOR THE PLACEMENT OF SOLID MATERIALS

This application claims the benefit of U.S. Provisional Application Ser. No. 60/026,911, filed Sep. 27, 1996 now abandoned.

The present invention concerns a device for inserting or implanting a solid or other semi-solid implant(s) or pellet(s) under the surface of a tissue. More particularly, the present invention relates to a novel means for assuring that such implants can be reliably and uniformly placed into a desired position under or inside a particular layer of tissue, most preferably under the skin of a mammal, substantially parallel to the surface of the tissue.

BACKGROUND OF THE INVENTION

The prior art provides a number of mechanisms for implanting materials, particularly medically applicable materials, in an animal. U.S. Pat. No. 4,451,253 (Harman) teaches an implant injector with a stable obturator held secured within the injector body and a retractable, hollow needle or trocar. In its initial position the needle is extended such that an implant rests inside the needle against the distal end of the stable obturator. After the needle is injected into the desired position, the retractable needle is withdrawn along the obturator to uncover and deposit the implant. U.S. Pat. No. 4,820,267 (Harman), U.S. Pat. No. 4,846,793 (Leonard et al.) and U.S. Pat. No. 4,994,028 (Leonard et al.) disclose devices with hollow, needle-like cannulas for implantation of a plurality of solid, elongated medicinal pellets. These devices are designed such that a user slides a manually engageable knob along the body of the instrument to move a plunger through the needle and dispense the pellets. U.S. Pat. No. 4,661,103 (Harman) teaches a similar device with a slotted barrel element to slidably mount an integral magazine for multiple implant pellets. U.S. Pat. No. 4,871,094 (Gall et al.) provides an implantation device which utilizes a syringe-like, distally-protruding coaxial plunger and a side-loading opening for placing implants in the injector. The Gall et al. devices also include a staggered channel passing through the external surface of the device's body, with each section of the channel corresponding roughly in length to that of the implants. A laterally protruding knob on the plunger slides between points within the staggered channel to facilitate implantation of one pellet at a time. U.S. Pat. No. 4,900,304 (Fujioka et al.) teaches another standard plunger, side-loading implantation device. The Fujioka et al. device differs in its side-loading activity from that seen in the Gall et al. device, above, in that the loading port is located in the side of the device's needle or trocar member, which is loaded with implants prior to being inserted into the body of the injector. U.S. Pat. No. 4,402,308 (Scott) describes an implant injector having a hollow, slotted needle or trocar rotatably mounted inside a sheath, the sheath being retractable to expose any portion of the slotted needle. U.S. Pat. No. 4,941,874 (Sandow et al.) provides for a transparent implantation device with a protective covering to protect the plunger rod and prevent it from falling out. U.S. Pat. No. 4,753,636 (Free) teaches a syringe-style implant injector in which a tab-like clip is releasably secured to positions on the obturator to regulate its forward progress and limit each implantation to a single implant pellet. U.S. Pat. No. 4,147,164 (Behney) directs a method of placing shape correcting implants into canine ears. Finally, U.S. Pat. No. 5,385,554 (Brimhall) teaches a wing-shaped pair of extensions for a catheter inducer which facilitates the gripping of the needle.

In addition, the prior art has addressed some means and methods for inserting devices into tissues at reasonably prescribed angles. U.S. Pat. No. 2,577,481 (Piechaczek) set forth an apparatus comprising, generally, a flattened base to be placed against a patient's skin and adjustable means for altering the angle at which a hypodermic needle passes through the plane of the base. Similarly, U.S. Pat. Nos. 5,024,665 and 4,966,589 (both to Kaufman) describes a composite catheter assembly which secures the body and needle of an inserting device such that its angle of penetration into the body is substantially maintained during operation. U.S. Pat. No. 5,192,271 (Kalb et al.) discloses a device for delivering an injection to a penis, the device comprising a ring designed to encircle the penis, the ring having one or more tubular extensions protruding from the ring such that a hypodermic needle passing through the tube and ring is guided to the central erectile tissue. U.S. Pat. No. 5,395,317 (Kambin) provides a method of treating a herniated disc, the method including a jig which utilizes substantially parallel channels in a jig and an original guide passing through one channel to align subsequent linear devices and direct them toward the desired location in relation to the disc. U.S. Pat. No. 4,403,987 (Gottinger) discloses an injection aid comprising, in general terms, a hypodermic syringe, an angled ramp means, and a slidable base, the base being designed to secure the syringe and slide down the ramp means at the prescribed angle to make a desired injection into a limb. U.S. Pat. No. 3,324,854 (Reese) and U.S. Pat. No. 2,660,169 (Malm) disclose syringe attachments which protrude from the needle end of a syringe and allow the user to guide the syringe's needle into a specified, upraised portion of skin. Finally, U.S. Pat. No. 5,300,079 (Niezink et al.) teaches a spring operated injector designed to implant objects such as transponders used for identifying hogs. The injector utilizes a positioning means comprising a pin which is set against a body as a guide for an insertion needle to be passed parallel to the pin and into and out of the body.

While the devices of the prior art provide means for inserting a solid subcutaneous implant into a patient or certain means for determining the angle at which an injection or implantation is made, none limits the angle of insertion such that the device or materials they are designed to implant can be placed only at the desired depth underneath and substantially parallel to the surface of the tissue.

BRIEF DESCRIPTION OF THE INVENTION

The prior art, as demonstrated above, teaches a number of devices for implanting subcutaneously solid materials, such as solid contraceptive capsules. While most such implants are intended to be placed directly under the skin, incorrect utilization of the prior art devices can result in the implantation of the solids in deeper tissues. Similarly, insertion of a subcutaneous pellet(s) or implant(s) can result in unintended placement at varying, rather than standard, distance from the site of trocar puncture. Location and removal of improperly deposited implants can present a challenge during a removal process and discomfort to the implant recipient. The present invention provides an injecting or implanting device designed to facilitate the deposition or implantation of solid material or materials under and relative to the plane or surface of tissues.

In general, the present invention comprises an insertion or implantation device or injector for inserting, implanting or depositing solid or semi-solid implants or pellets under the surface of a tissue, most preferably mammalian skin, the device comprising:

a) a housing or body to support the elements of, and coordinate the actions of, the insertion device or injector;

b) a hollow tubular member secured via its proximal end to the housing or body, the hollow tubular member being optionally, and preferably, sharpened at its distal end;

c) a channel or passage running coaxially through the housing or body and the hollow tubular member, the channel or passage having sufficient internal dimensions to accommodate the storage and passage of the relevant solid or semi-solid materials or pellets;

d) an obturator or rod of sufficient length and dimensions to pass through the channel or passage through the housing and tubular member to facilitate passage of the solid materials therethrough; and e) a tissue penetration guide, the guide extending from the housing or body as a substantially linear, preferably linear, extension of material maintained parallel to and separated by a distance from the hollow tubular member, the distance preferably approximating the thickness of the tissue under which the implant will be deposited The insertion device or injector may also optionally have corresponding means on the obturator and on or in the housing or body to regulate movement of the obturator through the passage. In another optional embodiment, the corresponding means serve to facilitate or allow only one-way motion of the obturator through the channel or passage. While some amount of flexibility may be desirable for some devices and uses, it is generally preferred that the tissue penetration guide be formed from a rigid material or combination of materials.

In a preferred embodiment, an insertion device or injector for solid materials of the present invention comprises:

a) a housing or body;

b) a hollow tubular trocar secured via its proximal end to the housing or body, the hollow tubular member being sharpened at its distal end;

c) a channel or passage running coaxially through the housing or body and the trocar, the channel or passage having sufficient internal dimensions to accommodate the storage and passage of the relevant solid materials;

d) an obturator or rod of sufficient length and dimensions to pass through the channel or passage through the housing and tubular member to facilitate passage of the solid materials therethrough; and e) a tissue penetration guide, the guide extending from the housing or body as a linear extension of material maintained parallel to and separated by a distance from the trocar, the distance preferably approximating the thickness of the tissue under which the solid materials will be deposited.

In a more preferred embodiment, the implantation devices just described may further comprise one or more means in, on or associated with the length of the obturator or rod and one or more means in, on or associated with the housing or body which act to facilitate one-way or uni-directional movement of the obturator or rod through the channel or passage. In a further preferred embodiment, the means which facilitate the one-way motion of the obturator through the device comprise means which, without exceptional proximally drawn force on the obturator, prevent the obturator from being withdrawn beyond predetermined positions along its length.

BRIEF DESCRIPTION OF THE DRAWINGS

FIG. 1 provides a cross-sectional side view of an insertion or implantation device of the present invention.

FIG. 2 is a cross-sectional side view of an insertion or implantation device of the present invention being inserted through a recipient's skin.

DETAILED DESCRIPTION OF THE INVENTION

Figure 3:
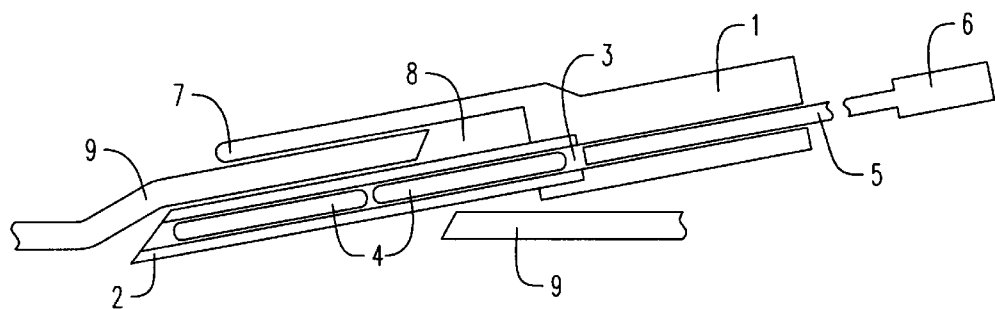
FIG. 3 is a cross-sectional side view of the insertion or implantation device of FIG. 2 directed properly into a subcutaneous location.

Devices of the present invention can be readily understood from the embodiments set forth in FIGS. 1–5. FIG. 1 provides a cross-sectional side view of an insertion or implantation device of this invention comprising a housing (1) coupled to a trocar (2) such that a channel or passage (3) passing coaxially between them allows passage of materials, preferably solid materials, through the implantation device. FIG. 1 further illustrates two solid implants (4) located in the trocar (2). An obturator or rod (5), shown with an optional enlarged finger grip (6), can be used to move the materials through the channel (3), preferably from the proximal or housing (1) end of the implantation device to and through the distal or trocar (2) end. For the purposes of this disclosure, the term distal is used to refer to those portions of the device normally held away from the operator during use, such as the open end of the hollow tubular member, and proximal refers to those portions of the device normally held toward the operator during use, such as the optional enlarged finger grip (6).

FIGS. 1–3 also illustrates a tissue or skin penetration guide (7) extending distally from the housing (1) substantially parallel to and separated from the trocar (2) by a space or gap (8). The penetration guide is preferably rigid and relatively inflexible and serves to limit the depth and extent to which the distal end of the devices hollow tubular member can be inserted under a tissue corresponding to the depth and extent desired for the procedure. As illustrated in FIG. 2, insertion of the trocar (2) through the skin (9) at an undesirably steep angle causes the distal end of the penetration guide (7) to contact the surface of the tissue or skin and inhibit further forward motion at that angle. If the device is lowered to a more acceptable angle (FIG. 3) the trocar (2) can be inserted under the skin (9), with the tissue (9) immediately over the channel of insertion passing in the space (8) between the trocar (2) and the penetration guide (7).

Throughout the insertion of the trocar, it is preferred that the obturator (5) be maintained at a position within the device's internal passage (3) that holds the solid materials at the distal end of the passage (3) during insertion into the recipient Deposition of the solid material (4) in the channel created by the insertion can then be accomplished by maintaining the obturator (5) in its position and drawing the remainder of the insertion or implantation device backwards or proximally along the length of the obturator (5). In cases where a single pellet or bolus of solid material is being deposited, the device's trocar (2) may be pulled free from the recipient during this proximally-directed motion. In some instances, it may be preferable to utilize an obturator (5) of sufficient length such that the obturator's distal end maintains contact with the deposited solid material until after the trocar (2) has been fully withdrawn from the recipient. For depositions of columnar solids, such as those depicted in FIGS. 1–3, it is generally sufficient that the obturator (5) be of sufficient length to reach substantially to the distal end of the trocar (2). As the trocar (2) is withdrawn back from the solid implant, the surrounding tissues will begin to return to their original position and detain the implant in position. In depositing a plurality of such materials, more than one insertion may be desired. The first insertion can be made to a position allowing the just mentioned process to deposit the first piece or bolus of solid material. As the distal end of the trocar (2) is drawn back near the initial opening in the tissue, and after the first deposition has been accomplished, the device can be turned so that another insertion can be made to the side of the initial deposit. By repeating these steps a series of depositions can be made radiating from a single point of insertion through the skin (9). A more thorough description of this type of radiating deposition utilizing the solid Norplant® levonorgestrel implants of Wyeth-Ayerst Laboratories can be seen at pages 2699 and 2700 of the 1995 Physician's Desk Reference (49 Ed.), published by Medical Economics Data Production Company at Montvale, N.J. 07645-1742.

It is most preferred that the devices of the present invention further utilize one or more means to facilitate one-direction motion of the obturator through the channel or passage. More specifically, it is preferred that the device have one or more means on the obturator and on or in the housing or body that act together to facilitate the proximally-directed movement of the housing (1) and trocar (2) along the obturator, i.e., while the obturator is held steady, the housing and trocar may be drawn proximally in one or more defined segments backward along the obturator for the purpose of uni-directional movement of materials through the housing (1) and trocar (2) for implantation. With this in mind, one skilled in the art will understand that any number of means and designs can be used to accomplish this restriction in obturator movement.

Figure 4:
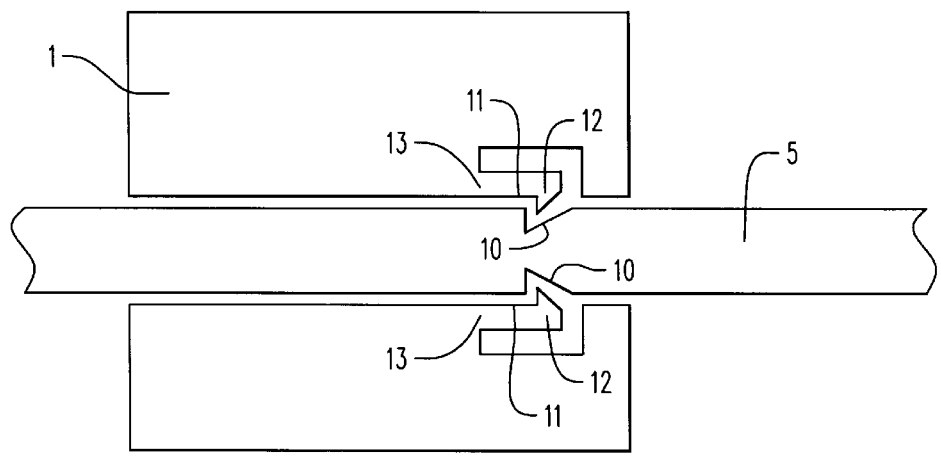
FIG. 4 is a cross-sectional top view of an embodiment of one means for assuring uni-directional movement of an obturator through the body of an insertion or implantation device of the present invention.

One example of such means is illustrated in the cross-sectional, top view of FIG. 4. In this embodiment, indentations (10) at set positions in the obturator (5) correspond to one or more biased protrusions (12) projecting from the housing (1), the protrusions (12) extending into the channel (3) on a biased arm (11). While not shown in the view of FIG. 4, the biased arm (11) is secured to the housing only via the juncture with the housing (1) noted with the number (13) and is free to move and flex from a first position in which the protrusion (12) extends into the channel (3) and a second or retracted position in which the protrusion extends into the channel less than in the first position. The obturator (5) for this embodiment has sufficient dimensions to contact the protrusions (12) and force the biased arms into their second or retracted position as the obturator passes through the channel (3). Only when aligned with an indentation (10) in the obturator (5) does the protrusion become less impinged or reversibly displaced by the side of the obturator (5) such that the biased arm (11) can spring back into its first position or a position corresponding more to the first position. At this point the protrusion (12) is situated in the indentation (10) and retraction of the obturator is inhibited or, preferably, prevented by contact of the relatively flat distal surfaces of the protrusion and the indentation.

In one embodiment of the present invention the indentations (10) in the obturator (5) may be separated by a distance corresponding to the length of an implantable solid or bolus of material. In another embodiment the indentations (10) may be closer together to more stringently restrict backward or proximally directed motion of the obturator relative to the housing (1).

Other conventional means of limiting or assisting in the preferred uni-directional movement of an obturator (5) through a housing (1), channel or passage (3) within the scope of this invention will be understood by those skilled in the mechanical arts. The biased arms (11) and protrusions (12) of FIG. 4 can be substituted with other series of mechanical catches, slots, indentations, protrusions, biased or spring-operated mechanisms, etc. which act between some portion of the obturator and some portion of the housing or channel wall to suggest, facilitate, or maintain uni-directional movement of the obturator through the device. For some devices within the scope of this invention it may be desired that the uni-directional motion of the obturator through the device be capable of being overridden in certain instances, i.e. that the obturator be capable of being drawn backward (proximally) toward the operator after forward (distal) progress has been made. This may be accomplished by conventional means, such as the means illustrated in FIG. 4 wherein the molded material of the biased arm (11) is comprised of a composition, width and thickness which allows it to be biased away from the obturator by a sufficient proximal (backward) motion of the obturator and the resulting contact between the biased projection (12) and the distal wall of the obturator's indentation (10). In another embodiment, the indentations in the obturator and the protrusions on the biased arm have more rounded dimensions at the points where they meet and interact. Such rounded means would have less ability to catch on each other and could be more readily overridden, if necessary.

In the embodiment illustrated in FIG. 4, the indentation (10) in the obturator (5) is defined by a forward or distal wall which is substantially perpendicular to the side of the obturator. At the deepest portion of the indentation a sloping or ramped wall angles proximally to meet the side of the obturator. The protrusions (12) on the biased arms (11) are designed such that, when they are aligned with and enter the indentations (10), physical contact between the protrusions (12) and the perpendicular distal wall of the indentation (10) inhibit or prevent retraction of the obturator relative to its initial progress through the housing (1).

It is understood that any equivalent means may be utilized to accomplish the just described interaction between the housing and the obturator. The mechanism or means for inserting a protrusion associated with the housing into an indentation or invagination in or associated with the obturator may comprise a molded extension of the housing, as illustrated in FIG. 4, or it may be a separate mechanism held in association with the housing. In FIG. 4, this means is shown inside the housing (1), adjacent the channel (3). It may be located at any location which allows the desired action and does not inhibit the activity of the device. It will also be understood that within the scope of this invention are similar means in which one or more projections, biased or otherwise, on the external surface of the obturator (5) interact with invaginations, indentations, or other means on or associated with the housing to facilitate uni-directional movement of the obturator through the housing, or the housing and trocar backwards (proximally) along the obturator.

The mechanisms of the protrusions (12), biased arm (11) and indentations (10) in the obturator (5) may serve another function, in addition to limiting the motion of the obturator. They also can serve to communicate with the operator the position of the obturator (5) in the housing (1) and the extent to which the solid materials have been deposited. In the case of solid pellets (4) of designated length, such as those in FIG. 4, it is preferable that the indentations (10) be spaced relative to the length of material being deposited. After insertion of the device's trocar (2), the operator withdraws the housing (1) proximally along the length of the obturator (5). A first indentation (10) can be placed in the obturator (5) such that it will encounter and act with its corresponding protrusion (12) at the point in which the first solid pellet (4) has passed from the distal end of the implantation device and been deposited in the desired location. As the operator draws the housing back along the obturator, the friction created by the interaction of one or more protrusions (12) on the side of the obturator (5) will allow a reasonably uniform motion recognized by the operator. This uniform motion will cease as the protrusions (12) and indentations (10) align and be recognized as such by the operator. Predetermined spacings of indentations can be used in this manner to identify and regulate the implantation of a plurality of solids.

In another embodiment, mechanisms similar to those just described may be utilized to notify an operator of the progress of the implantations through implantation devices in which uni-directional movement of the obturator is not preferred. Devices of this type may utilize the action created by the biased arms (11), protrusions (12) and indentations (10) just described, with the protrusions (12) and indentations (10) having morphologies and dimensions which reversibly interact. In one instance, the protrusions (12) could be maintained substantially as shown in FIG. 4, with the indentations being angled or ramped distally, as well as proximally, to allow motion of the protrusion (12) in either direction. In another instance, the protrusion and indentations could be rounded such that no angles on either means could contact the other to create an insurmountable barrier to motion of the obturator, proximally or distally.

The hollow tubular members of the present invention may comprise any tubular form which acts as a cannula and allows the desired function of the insertion or implantation device. For devices to be inserted into a pre-existing opening in the tissues in question, a distally blunted tube may be desired. If the device is to make its own opening in the tissue, a pointed and/or sharpened distal end on the tubular member would be preferred. The hollow tubular member may be a molded extension of the housing or, as illustrated in FIGS. 1–3, it may be a separate entity secured to the housing (1). The tubular members may also be made of any material which is sufficiently rigid to make the desired insertion and does not create undesirable effects on the surrounding tissues. In the most preferred embodiment of this invention, the hollow tubular member comprises a hollow cannula, hypodermic needle or stainless steel trocar sharpened by angular cross-section at its distal end and inserted into the housing as illustrated in FIGS. 1–3. For the purposes of this disclosure, the term "trocar" refers to a distally sharpened, tubular member, preferably of stainless steel, secured to the housing via its proximal end. The trocar is most preferably designed to be maintained connected to the housing and is not intended to be left in or under a tissue after the deposition or implantation has been accomplished.

The hollow tubular member may also be secured to the housing by any means practicable. For instance, it may be held to the housing by an adhesive, such as a medically acceptable epoxy. The proximal end of the hollow tubular member may also be configured such that the housing portion may be molded around it. For instance, the tubular member may be flared outward or have an outwardly projecting flange or one or more projections at its proximal end which may be encased by a molded housing.

The hollow tubular member may also have additional elements which are particularly useful when the device is used for multiple insertions and deposits. The first is a visible line, mark, score, upraised portion or other indicator associated with the external surface of the tubular member, near the tubular member's distal end. This visible indicator may be utilized to inform the operator, while the tubular member is being withdrawn from a tissue, when the distal end of the tubular member is nearing the opening in the tissue. If an additional insertion is desired, the operator can then rotate the implantation device out of the line of the initial insertion and reinsert the device along another line. Such lines may be placed on or in the material of the tubular member by any means practicable and which will not interfere with the desired action of the device. If the tubular member is a molded unit, the line, mark, score, upraised portion, etc. may be molded into the surface of the material. In devices where the tubular member is a stainless steel cannula or trocar, it is preferred that the visible indicator be laser etched into the surface of the cannula or trocar.

Another element of use with an implantation or insertion device for multiple solid implants is an opening through the side of the hollow tubular member, preferably at the point making the first and second solid implants visible through the opening. This opening is intended to be sufficient to allow the solid implants to be viewed, but not pass through the opening. Prior to use, this opening allows the operator to quickly confirm that the implants are in place. As the obturator progresses through the hollow tubular member it will reach the opening and be visible behind the final implant to serve as notification thereof. The opening may be formed in the side of the hollow tubular manner in any fashion and by any process which yields the desired opening without inhibiting the function of the device. If the tubular member is a molded unit, the opening may be molded as a space through the surface of the material. In devices where the tubular member is a stainless steel cannula or trocar, it is preferred that the opening or window be laser cut through the wall of the cannula or trocar.

The housing, itself, may also comprise any dimensions which allow the devices to be used as described herein, preferably with an ergonomically acceptable design facilitating use and user comfort. It may be made of more than one section coupled together to accommodate the penetration guide, trocar, obturator and, optionally, means for regulating motion of the obturator. Preferably, the housing will comprise a single unit, most preferably of medically acceptable molded polymer, such as a polyacrylic or nylon 66. It is also preferred that the hollow tubular member be joined to the housing substantially near the bottom surface of the housing, allowing the device to be held nearly parallel to the surface or general plane of the tissue into or under which it is being inserted.

The obturators useful with the devices of the present invention may comprise any form useful to pass solid materials through the passage or channel and, optionally, which has means designed to interact with means associated with the housing to halt or delay withdrawal of the obturator once it has reached certain positions in the channel. In its simplest form, the obturator comprises a substantially linear rod or column of material of sufficient length and rigidity to force solid materials through the length of the channel or passage. The obturator may have an enlarged portion or body on its proximal end to enhance the operator's grip, as indicated by structure (6) in FIGS. 1–3. In another preferred embodiment the distal end of the obturator is enlarged, preferably such that it occupies nearly all of the lateral cross-sectional area of the chamber as it passes through. This enlargement is particularly useful for instances in which the solid to be deposited is granular, particulate, or another form of non-compressed or non-contained materials. It will be understood that the insertion or implantation devices of the present invention may be used with any solid or semi-solid material that may be retained within and pass through the channel or passage of the device. These may include, but are not limited to, the solid pellets, granular and particulate forms already mentioned, as well as powders, gels, creams, foams, encapsulated liquids, sponges, etc. For most uses and for economy of production, it is preferred that the obturator, like the housing, be formed of a reasonably rigid polymer, such as through reaction injection molding techniques.

The channel or passage through the housing and hollow tubular member may be of any design which is allows solid materials to pass through and be deposited as intended. It is preferred that the channel or passage have substantially the same internal dimensions throughout its length. More preferably, the channel is substantially tubular and rounded or circular in lateral cross-section throughout its length.

The tissue penetration guides (7) useful with the present invention may comprise any design which may be maintained substantially parallel to the hollow tubular member, separated from the tubular member by the appropriate distance for the relevant insertion procedure, and allows passage of tissue between the guide and tubular member. The guide may be narrower or wider than, as well as longer, shorter or the same length as, the hollow tubular member. The guide may be coupled, releasably or not, to any portion of the device, and coupled in any manner, which allows the desired actions. The guide is preferably a solid, molded extension of the housing or body. The penetration guide may comprise a plurality of substantially parallel extensions from the housing or body, each substantially parallel to the hollow tubular member. Most preferably, the penetration guide is a single extension. The penetration guide may also be designed to allow only a single distance between itself and the device's hollow tubular member or it may be adjustable to allow the operator to set the distance between the two according to the thickness of tissue in question.

The distance or gap between the penetration guide and the hollow tubular member may be any separating distance which allows the tissue to pass between the two and limits the insertion of the hollow tubular member to the desired depth under the tissue or tissues. When the tissue is human skin and the insertion is designed to make a subcutaneous deposit, as in the case of solid contraceptive implants, it is preferred that the penetration guide is separated from the hollow tubular member by a distance of between about 0.05 and about 0.10 inches, more preferably between about 0.075 inches and about 0.095 inches, and most preferably by a distance of between about 0.080 inches and about 0.090 inches. It will be understood that by adjusting the gap or distance between the penetration guide and the hollow tubular member devices of this invention can be utilized with other tissues including, but not limited to, pericardium, pleura, liver capsule, etc.

Figure 5:
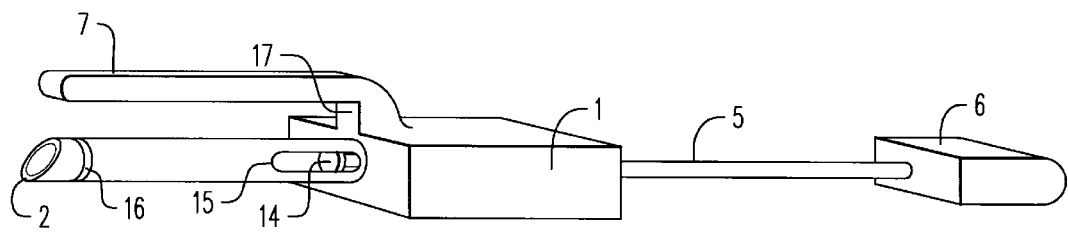
FIG. 5 is a three-dimensional side view of one insertion or implantation device of this invention.

FIG. 5 provides a three-dimensional side view of an implantation device of this invention with some of the embodiments described herein. The implantation device comprises a housing or body (1) with a distally sharpened trocar (2) and a slightly shorter penetration guide (7) passing parallel to each other from the housing (1). The implantation device's obturator (5) has an enlarged proximal end (6), serving as a finger grip, and an enlarged distal end (14) to facilitate full passage of solid materials through the implantation device. The trocar (2) contains an opening or viewing window (15) to allow the operator to view the material in the implantation device's channel. One or more visible indicators on the outside of the trocar, such as the visible line (16) encircling the trocar just proximal to its distal end, can serve to notify the operator of the trocar's position as it is inserted into or withdrawn from a tissue. Particularly for devices designed to implant, inject or insert a single solid mass or a single bolus of solid material, the distal surface of the device's body (17) can be used to limit the extent to which the trocar (2) may be inserted into or under a tissue. As the body of the housing (1) is most preferably larger than the insertion into which the trocar is placed, it will contact the tissue in question and prevent further insertion of the trocar. If the mass of solid material to be deposited can be contained in the portion of the trocar (2) that extends from the housing (1), contacting this distal face (17) of the housing (1) against the tissue will indicate that the mass of solids to be deposited are in a fully inserted position.

What is claimed:

1. A device for subcutaneously depositing a solid material, the device comprising:
   a) a housing;
   b) a trocar having a sharpened distal end, a proximal end and a length sufficient to subcutaneously deposit the solid material, the trocar being secured via its proximal end to the housing;
   c) a tubular channel running coaxially through the housing and the trocar, the tubular channel having internal dimensions to accommodate the storage and passage of the solid material;
   d) an obturator having a length and dimensions to pass through the tubular channel through the housing and trocar to facilitate passage of the solid material therethrough;
   e) one or more grooves in or associated with the length of the obturator;
   f) one or more biased members coupled to the housing, with each biased member having a biased arm and a protrusion, the biased arm reversibly extending the protrusion into the tubular channel to interact with the one or more grooves in or associated with the length of the obturator to facilitate a uni-directional movement of the obturator through the tubular channel; and
   g) a tissue penetration guide, the penetration guide extending a length from the housing as a linear extension of material maintained parallel to and separated by a distance from the trocar, the length of the trocar, length of the penetration guide and the distance between the trocar and the penetration guide being sufficient to:
      i) allow the tissue to pass between the trocar and the penetration guide; and
      ii) allow the trocar to be fully inserted into or under the tissue; and
      iii) to limit the angle and depth of insertion of the trocar into or under the tissue.

2. The device of claim 1 wherein the penetration guide is separated from the hollow tubular member by a distance of between about 0.05 inches and about 0.10 inches.

3. The device of claim 1 wherein the tissue penetration guide is separated from the trocar by a distance of between about 0.075 inches and about 0.095 inches.

4. The device of claim 1 wherein the tissue penetration guide is separated from the trocar by a distance of between about 0.080 inches and about 0.090 inches.

5. The device of claim 1 in which the tissue penetration guide extends from the housing substantially parallel to the trocar and terminates at a point substantially corresponding to the distal end of the trocar.

6. The device of claim 1 in which the trocar projects from the housing beyond the distal end of the tissue penetration guide.

7. The device of claim 1 in which the tissue penetration guide projects from the housing beyond the distal end of the trocar.

* * * * *